US00PP08519P

United States Patent [19]

Leadbeater

[11] Patent Number: Plant 8,519

[45] Date of Patent: Dec. 28, 1993

[54] HAMPSHIRE APPLE TREE CULTIVAR

[76] Inventor: Erick Leadbeater, Rte. 1, Box 444, Contoocook, N.H. 03229

[21] Appl. No.: 917,790

[22] Filed: Jul. 20, 1992

Related U.S. Application Data

[63] Continuation of Ser. No. 632,071, Dec. 21, 1990, abandoned.

[51] Int. Cl.[5] ..... A01H 5/00

[52] U.S. Cl. ..... Plt./34.1

[58] Field of Search ..... Plt./34.1

*Primary Examiner*—James R. Feyrer

*Attorney, Agent, or Firm*—Fish & Richardson

[57] ABSTRACT

A new and distinct variety of apple tree which has a superior growth habit ideal for productive, dense plantings. The tree produces very attractive fruit in both shape and color. The apple is firm, crisp, juicy, and has very good eating qualities.

6 Drawing Sheets

This is a continuation of application Ser. No. 07/632,071 filed Dec. 21, 1990, now abandoned.

SUMMARY OF THE INVENTION

The present invention relates to a new and distinct variety of apple tree which was discovered by me in 1978 while growing as a seedling in a vacant tree space in a row in my cultivated orchard in a block containing several varieties of apples including Red Delicious, Macintosh, and Cortland on seedling root stocks located on Gould Hill Road in The Township of Hopkinton, County of Merrimack, State of New Hampshire.

I was attracted to the new variety by its uniquely desirable growth habits and its well colored firm fruit. The new variety exhibits outstanding tree shape with well spread and spaced branching making it ideal for central leader intensive plantings. The fruit is very attractive in texture, shape, color, and flavor.

Asexual propagation (by top-work grafting of Macintosh trees on Malling 7 rootstocks in 1982, top-work grafting of Cortland and Red Delicious trees on Malling 26 in 1983, and budding on Malling 26 in Stanley, N.Y., in 1987) has demonstrated that the unique characteristics of this new variety come true to form and is established and transmitted through succeeding propagation. The specimens described herein are growing in my cultivated orchard at Gould Hill Road, Township of Hopkinton, County of Merrimack, State of New Hampshire.

The new variety has been named the "Hampshire" cultivar.

BRIEF DESCRIPTION OF THE PHOTOGRAPHS

FIG. 1 is shows a tree and detail of the trunk with upright leader and well spaced, wide angle scaffold branches;

FIG. 2*a* shows a tree at harvest time with uniform fruit, while FIG. 2*b* shows a closer view of a tree at harvest time with uniform fruit;

FIG. 3*a* shows a tree at early bloom, while FIG. 3*b* shows detail of bloom;

FIG. 4 shows fruit and foliage; and

FIGS. 4*a*, 4*b*, 4*c* and 4*d* show detail of fruit, and FIG. 4*e* shows detail of foliage.

The figures show the tree, foliage, bloom and fruit in color as true as is reasonably possible.

DETAILED DESCRIPTION OF THE NEW VARIETY

Tree:

*Growth.*—Vigorous; medium size; upright leader with well-spaced, wide-angled scaffold branches.

*Shoots.*—Slender; straight; reddish-brown on exposed surface, olive on shaded portion.

*Shoot tip.*—Erect.

*Internodes.*—Long.

*Lenticels.*—Few, small, elongated, whitish.

*Pubescence.*—Medium and fine.

*Discussion.*—The tree tends to develop a natural, strong central leader or trunk with numerous laterals that develop into exceptionally sturdy scaffold limbs with crotch angles near 90° from the vertical leader. On younger trees, these laterals frequently develop distinct whorls. Heavy, early fruit production combined with the natrual spreading habit bring laterals to a nearly flat posture with minimal artificial limb positioning. Thus, the tree lends itself readily to central leader training with minimal pruning and training inputs. These numerous scaffolds over time would be rotated or thinned out, resulting in pruning scar as noted in FIG. 1.

Figure 1:
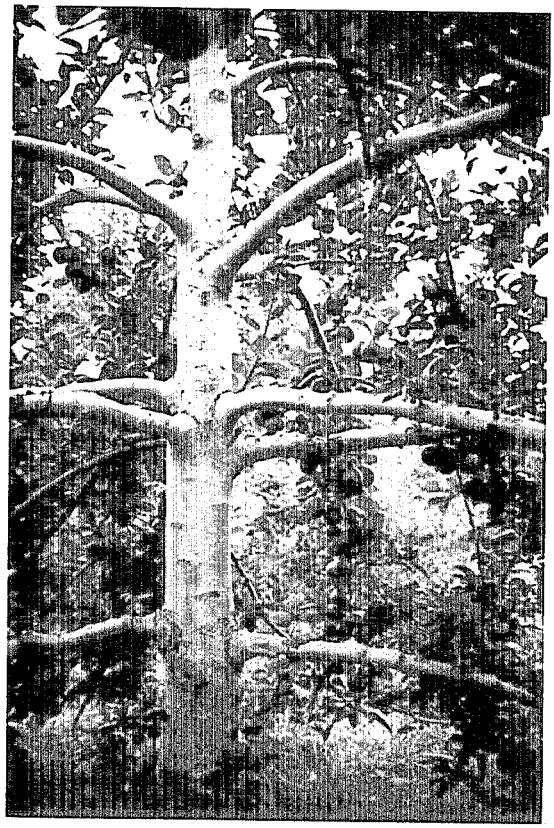

The crotch angles of scaffolds depicted in FIG. 1 of the original specimen are of natural origin. This tree has never received artificial limb spreading or tie downs. This natural spreading habit is enhanced by fruiting precocity.

Despite the flat posture trait of scaffolds, initation of water sprouts is not excessive, and those that do develop tend to spur heavily and fruit in their second or third years and, being supple, bend out under crop load. Water sprouts are not a problem with this variety.

Figure 2B:
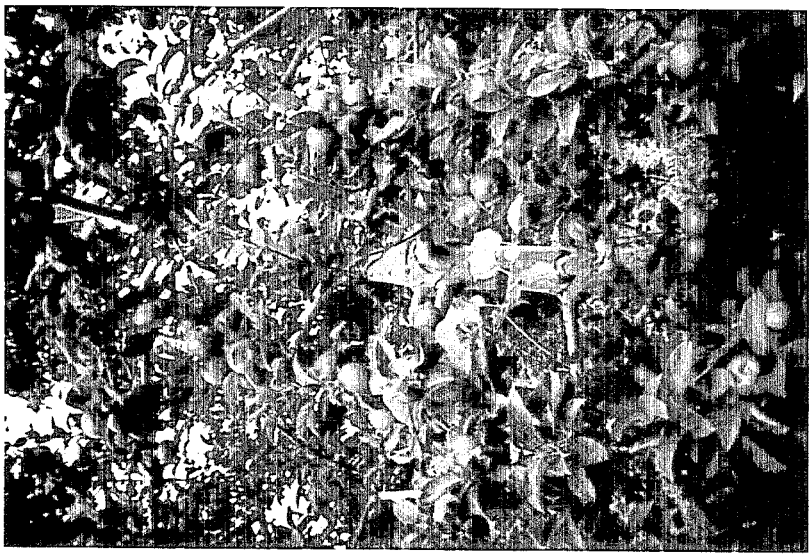
Figure 2A:
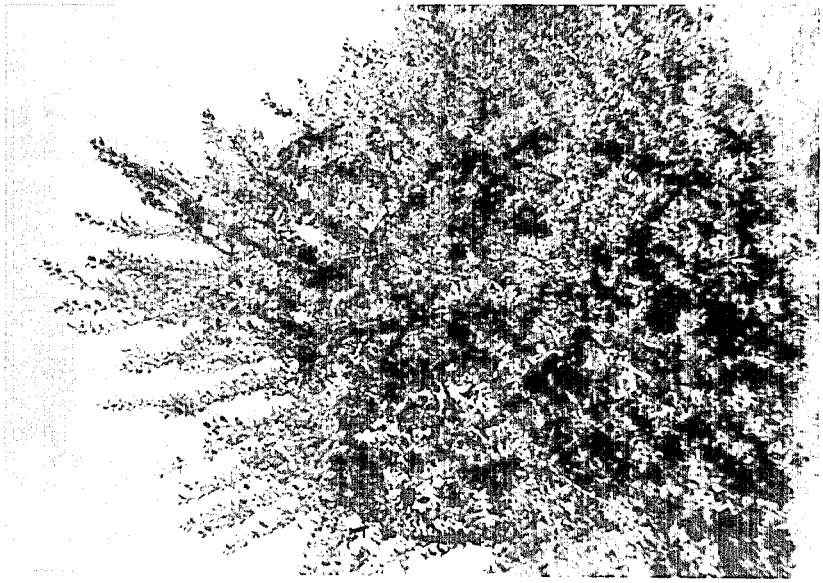
Figure 3B:
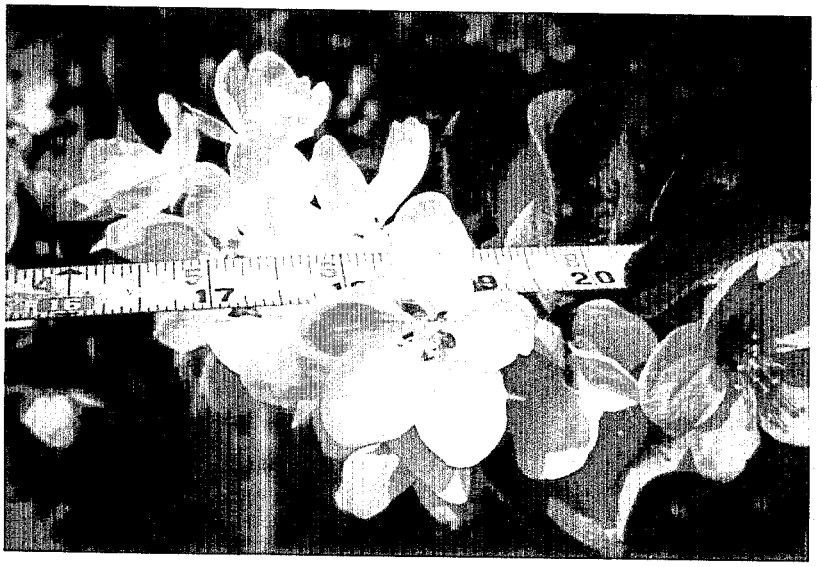
Figure 3A:
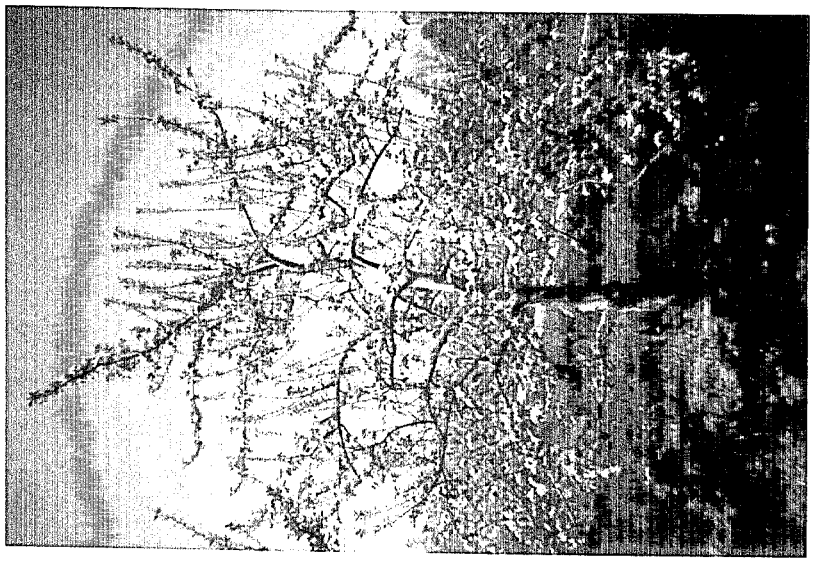
Figure 4:
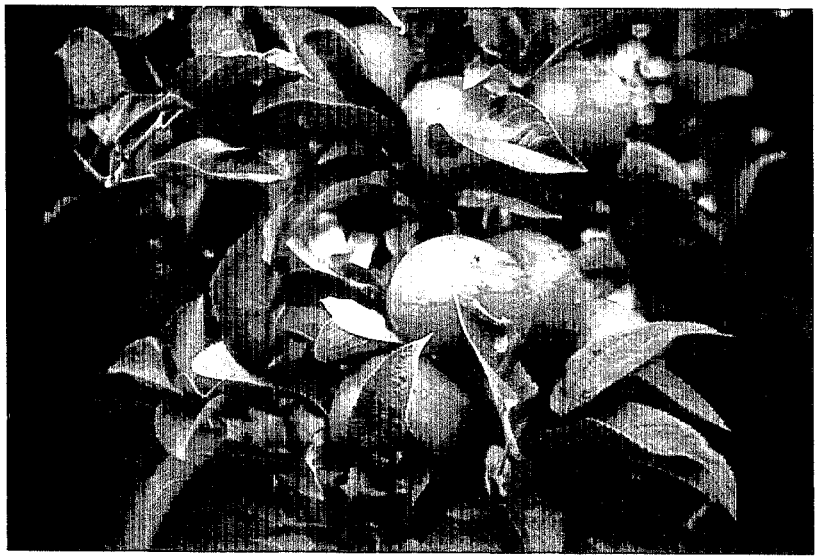
Figure 4E:
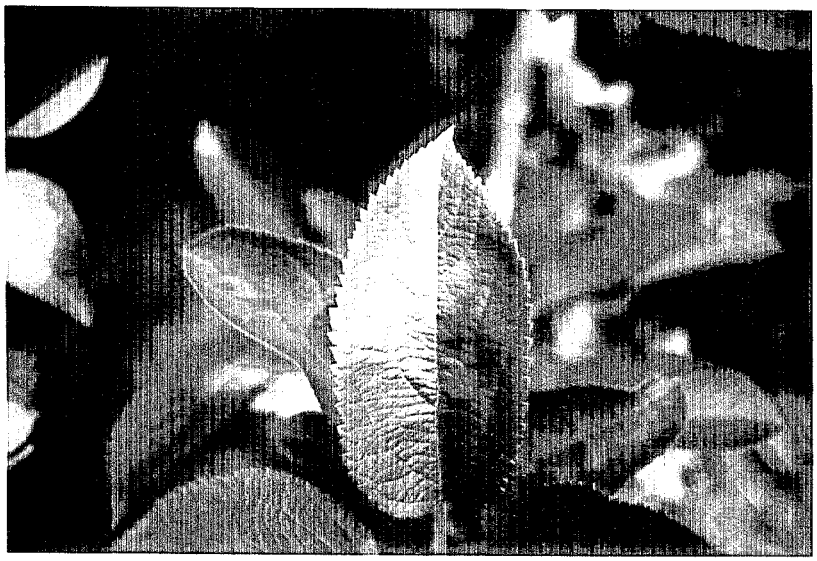
Figure 4A:
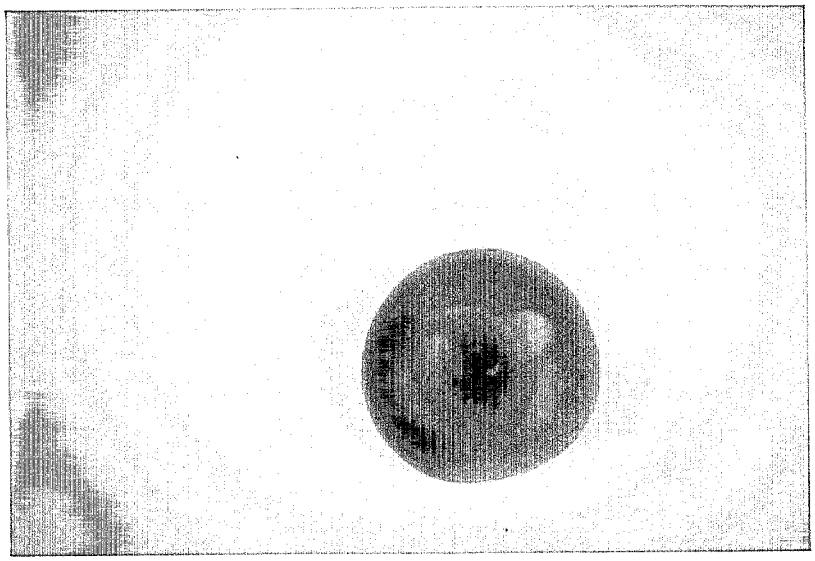
Figure 4B:
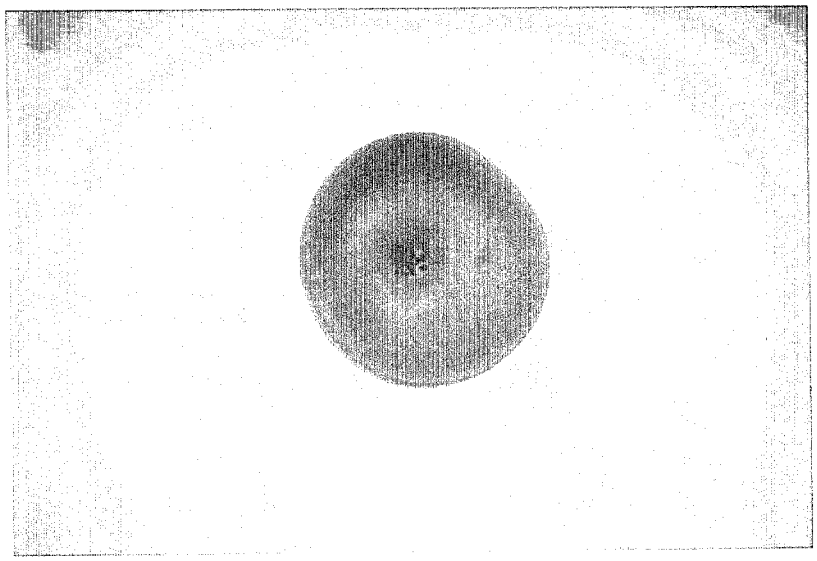
Figure 4C:
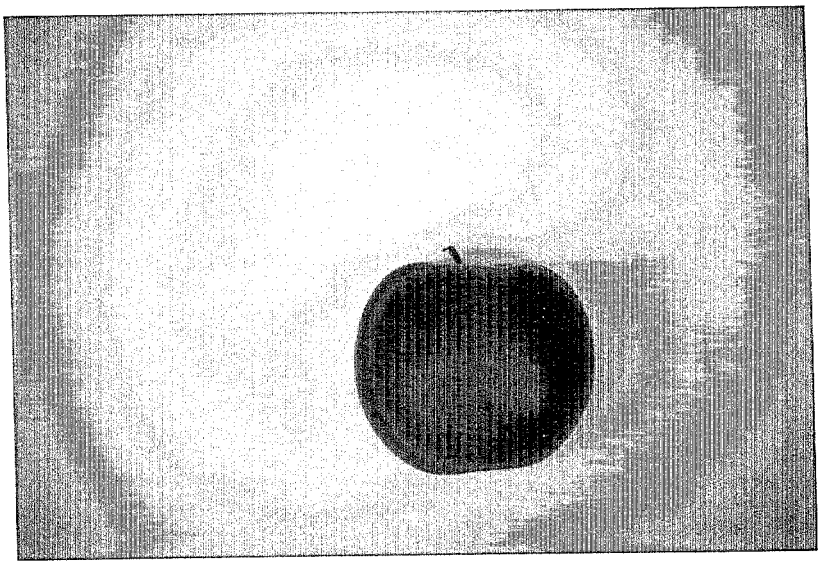
Figure 4D:
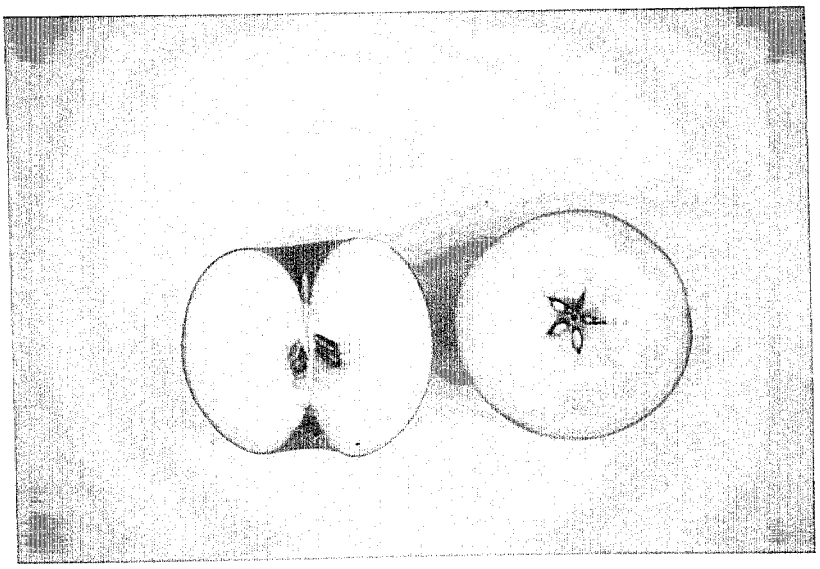

The figures presented are of the original specimen which is on its own roots and it is the only mature example of the tree. The number of vertical shoots as depicted in FIGS. 2*a* and 3*a* were encouraged and intentionally left over several years in an attempt to enlarge the canopy for production of bud wood for future propagation.

The actual age of the specimen is unknown, but it is at least 21 years. Its present height of under 17 feet and spread (width) of 16 feet is only 60% to 80% of a standard Macintosh tree of similar age and management on seedling roots.

Typical terminal growth on 4 year trees on M-26 rootstock is in the range of 25 cm to 60 cm, and on 9 year trees on M-26 is in the range of 20 cm to 35 cm. The usual internode range is 2½ cm to 3½ cm, with extremes from 2 cm to 4½ cm as a function of growing conditions.

The tree tends to fruit heavily early in life, primarily on fruiting spurs on 2 year and older wood, often producing "ropes" of fruit that size well. Even though fruit sizes well under these conditions, thinning is recommended, except in the densest plantings, to prevent this heavy cropping pattern from slowing canopy development. Heavily fruited limbs will bend below horizontal in response to crop load, yet breakage is uncommon, and no supplemental support is necessary.

Despite heavy cropping, with limited thinning, there is little tendency toward a biennial bearing habit. Chemical thinning of the original specimen to reduce clusters (more than one or two fruits per spur) has been readily accomplished with only one application of moderate concentrations of naphthalene acetic acid.

The bark of the tree is smooth up until 15 to 20 years of age and it is very similar to that of the Cortland cultivar with regard to both texture and color. Older bark exhibits the spalling habit of the outer layers similar to that of Macintosh. The color of flaked, mature bark ranges from "Cobweb" to "Rose Grey" (Plate 5, B - 7, to Plate 7, A - 8)[1]. The color of young (5 year) bark of moderate vigor ranges from "Roan" and "Domingo" to "Liver Brown" (Plate 7, J - 7 and 8 to H - 9). The color of the bark on terminal (1 year) wood of moderate vigor ranges from "Lava" through "Cordovan" to "Java Brown" (Plate 8, E - 7 through H - 8 to J - 8).

[1] All specific references to color provided herein are from Maerz and Paul. *A Dictionary of Color* (1950).

Leaves:

*Petiole.*—Medium to long, 3 cm to 5 cm (average about 4.1 cm), slender; 1½ mm average, with a variable red tinge of "Castilian Brown" to "Laurel Oak" ) Plate 7, J -9 and 10). This color usually fades to the "Light Stone" (Plate 12, J - 5) of the base of the central vein, but rarely may be carried part way up the central vein.

*Stipules.*—Small, erect.

*Blade.*—Medium in size, 6 cm to 10 cm long (average 7.9 cm), 4 cm to 5½ cm wide (average 4.7 cm); broad U-folded, oval in shape. Over time, variations in leaf color have been noted and, as with most varieties, these differences are strongly influenced by leaf maturity, exposure to sun and nutrition, particularly foliar feeding. Thus the following broad range of colors from "Verdure" through "Alfalfa" to "Light Chrome Green" (Plate 22, A to L - 12), "Wintergreen" through "Medium Brunswick Green" to "Medium Chrome Green" (Plate 23, A to H - 12), "Brunswick Deep Green" through "Evergreen" to "Chrome Deep Green" (Plate 24, A to H - 12). Colors are not unusual to the species.

*Leaf base.*—Full.

*Leaf apex.*—Full.

*Leaf tip.*—Short and acuminate.

*Leaf edge.*—Coarsely waved.

*Leaf reflection.*—Semi glossy to dull.

*Leaf color.*—Green with a bluish tinge.

*Vein color.*—In general, a light yellow that blends to the green of the leaf as the central vein progresses from petiole to tip. As noted with the petiole, there may be significant variation to be found, but a typical transition would be from "Light Stone" (Plate 12, J -5) to "Medium Chrome Green" (Plate 23, H - 12).

*Leaf surface.*—Bullate.

Leaf pubescence.—Short and light.

*Serrations.*—Serrate, regular, distinct but not sharp.

Flowers:

*Bloom.*—Medium early; abundant, large, white with pink center.

*Date of first bloom.*—May 16, 1989.

*Date of full bloom.*—May 18, 1989; generally within a day of the Macintosh cultivar.

*Discussion.*—Individual blossoms are very similar to those of the Macintosh cultivar, i.e. a pink bud color that transitions to almost pure white full bloom with a light "Peach Blossom" (Plate 1, C - 2) center. Flowers are generally about 2 mm larger than Macintosh, measuring about 4 cm in diameter. The bloom period for the specimen is about one day later than the Macintosh cultivar. Limited controlled pollination trials indicate successful fruiting of the specimen with Macintosh and Cortland pollen. Hampshire forms functional pollen as indicated by successful fruiting of protected Macintosh blossoms by pollen from the original specimen. Thus Macintosh and Hampshire appear to be cross compatible. The possibility of self-fruitfulness has not been ascertained.

Fruit:

*Maturity.*—Picked at our latitude from the last week of September through the second week of October (generally after Macintosh, with Empire and early Red Delicious season). There is little tendency to drop before maturity.

*Form.*—Roundish to ovate, symmetrical.

*Color.*—Fruit often colors prematurely by mid July with a solid red blush over 50% of the surface. This is unique in our area when compared with similarly-shaped cultivars like Empire, Macoun and Macintosh that mature with a solid red blush. Mature fruit color of the specimen is solid blush with no distinguishing striping and with only a light "bloom" on the surface. Full color of the fruit ranges from "Malaga", "Pompeii", "Anatolia", "India Red" and "Kazak" (Plate 7, L - 1, 2, 3, 6 and 9). Intensity of coloration seems to be season and sunlight-exposure dependent, and not necessarily a function of flesh maturity. Nearly 100% red blush on September 26.

*Skin.*—Smooth, thin and tough.

*Dots.*—Medium in number, small, whitish, depressed.

*Cavity.*—Narrow to medium in width, medium in depth, acuminate and symmetrical, occasional slight russeting.

*Stem.*—Medium in length and thickness.

*Basin.*—Medium in depth, wide, abrupt, smooth, symmetrical.

*Calyx tube.*—Long, wide, conical.

*Stamens.*—Marginal.

*Core.*—Large, closed, median.

*Seed cells and seeds.*—Seed cells are of moderate size in typical star pattern. Seed count, as with most varieties, is a function of climatic and pollination variables, but this variety typically has two seeds per cell with great uniformity held tightly in the seed cavity. Seeds are of medium size and acuminate, browning on maturity, with no particular distinguishing charcteristics.

*Flesh.*—The fruit flesh has a mild, pleasant, fruity bouquet, not heavily aromatic until very ripe. The flesh is creamy white, fine textured, very firm, crisp and juicy, with exciting eating qualities. Fruit flavor is sub-acid, yet mildly sweet; spritely, with a mild, fresh-fruit taste. On-tree storage of fruit is good. Fruit are moderately persistent with unharvested fruits hanging well into November, which is well beyond the harvest season at any latitude.

*Size.*—Uniformly $2\frac{3}{4}$ inches to $3\frac{1}{8}$ inches on mature tree, somewhat larger on young trees.

Keeping quality:

*Regular storage.*—Medium to long (up to 120 days).

*Controlled atmosphere.*—At least to June, flavor and texture maintained through both storage periods.

Use: Dessert, culinary.

Disease considerations: The tree and fruit exhibit little resistance to major diseases. The fruit and foliage are moderately susceptible to apple scab (Venturia inaequalis) and the fruit to sooty blotch (Gloeodes pomigena) in unsprayed trials. However, when treated with other regionally desirable cultivars, outstanding control of pests and pathogens is easily attainable with conventional integrated pest management techniques.

What I claim is:

1. A new and distinct variety of apple tree substantially as shown and described, particularly characterized by superior growth habit ideal for productive, dense plantings, very attractive fruit in both shape and color, that is firm, crisp and juicy, with very good eating qualities.

* * * * *